(12) United States Patent
O'Gorman

(10) Patent No.: US 10,226,440 B2
(45) Date of Patent: Mar. 12, 2019

(54) ORAL COMPOSITIONS COMPRISING CREATINE

(75) Inventor: Edward O'Gorman, Edinburgh (IE)

(73) Assignee: Eddie O'Gorman Ltd, Kilkenny (IE)

( * ) Notice: Subject to any disclaimer, the term of this patent is extended or adjusted under 35 U.S.C. 154(b) by 0 days.

(21) Appl. No.: 14/115,267

(22) PCT Filed: May 1, 2012

(86) PCT No.: PCT/GB2012/050955
§ 371 (c)(1),
(2), (4) Date: Nov. 1, 2013

(87) PCT Pub. No.: WO2012/150450
PCT Pub. Date: Nov. 8, 2012

(65) Prior Publication Data
US 2014/0066512 A1     Mar. 6, 2014

(30) Foreign Application Priority Data

May 4, 2011 (GB) .................................. 1107308.7
Jan. 23, 2012 (GB) ..................................... 1201012

(51) Int. Cl.

| | | |
|---|---|---|
| A61K 31/198 | (2006.01) | |
| A23L 2/39 | (2006.01) | |
| A61K 9/00 | (2006.01) | |
| A61K 9/06 | (2006.01) | |
| A61K 9/10 | (2006.01) | |
| A61K 31/197 | (2006.01) | |
| A61K 31/195 | (2006.01) | |
| A23L 29/238 | (2016.01) | |
| A23L 29/256 | (2016.01) | |
| A23L 29/269 | (2016.01) | |
| A23L 33/00 | (2016.01) | |
| A23L 33/175 | (2016.01) | |

(52) U.S. Cl.
CPC .............. *A61K 31/198* (2013.01); *A23L 2/39* (2013.01); *A23L 29/238* (2016.08); *A23L 29/256* (2016.08); *A23L 29/27* (2016.08); *A23L 33/175* (2016.08); *A23L 33/40* (2016.08); *A61K 9/0056* (2013.01); *A61K 9/06* (2013.01); *A61K 9/10* (2013.01); *A61K 31/195* (2013.01); *A61K 31/197* (2013.01); *A23V 2002/00* (2013.01)

(58) Field of Classification Search
CPC ............ A23V 2002/00; A23V 2200/33; A23V 2250/1842; A23V 2250/5026; A23V 2250/306; A23V 2250/506; A23V 2250/5086; A23L 1/0526; A23L 1/0532; A23L 1/0541; A23L 1/3051; A23L 2/39; A23L 1/296
See application file for complete search history.

(56) References Cited

U.S. PATENT DOCUMENTS

2001/0042936 A1    11/2001   Kessel
2004/0237663 A1*  12/2004   Farber et al. .............. 73/861.08

FOREIGN PATENT DOCUMENTS

| JP | 2007 209231 | 8/2007 |
|---|---|---|
| WO | WO 00/74500 | 12/2000 |
| WO | WO 03/026439 | 4/2003 |
| WO | WO 03/047367 | 6/2003 |

OTHER PUBLICATIONS

Shaheen et al, Biomed Mater Eng. 2004;14(4):371-82.*
Jager et al, Amino Acids (2011) 40:1369-1383.*
CreaphilTM by AngloSwiss, accessed on Apr. 28, 2015.*
Colombo et al., Observation of swelling process and diffusion front position during swelling in hydroxypropyl methyl cellulose (HPMC) matrices containing a soluble drug, Journal of Controlled Release 61 (1999) 83-91.
Hezave et al., Micronization of creatine monohydrate via Rapid Expansion of Supercritical Solution (RESS), Journal of Supercritical Fluids 55 (2010) 316-324.
Rae et al., Oral creatine monohydrate supplementation improves brain performance: a double-blind, placebo-controlled, cross-over trial, The Royal Society (2003) 2147-2150.
Powers et al., Creatine Supplementation Increases Total Body Water Without Altering Fluid Distribution, Journal of Athletic Training, vol. 38, No. 1 (Mar. 2003) 44-50.

* cited by examiner

*Primary Examiner* — Jean P Cornet
(74) *Attorney, Agent, or Firm* — Lodestone Legal Group; Jeromye V. Sartain

(57) ABSTRACT

The present invention relates to rehydration and nutritional products comprising creatine and/or its salts, or analogs or precursors thereof, in ready to use aqueous oral compositions, such as gels, pastes and the like, and products for reconstitution in water, for use by humans and animals, together with processes for their preparation and uses thereof.

15 Claims, No Drawings

ORAL COMPOSITIONS COMPRISING CREATINE

RELATED APPLICATIONS

This application is a U.S. national stage entry under 35 U.S.C. § 371 from International PCT application Ser. No. PCT/GB2012/050955 filed May 1, 2012 and entitled "Oral Compositions Comprising Creatine," which itself claims priority and is entitled to the filing date of British application Ser. No. GB 1107308.7 filed May 3, 2011, U.S. provisional application Ser. No. 61/521,840 filed Aug. 10, 2011, and British application Ser. No. GB 1201012.0 filed Jan. 23, 2012. The contents of the aforementioned applications are incorporated herein by reference.

The present invention relates to rehydration and nutritional products comprising creatine and/or its salts, or analogues or precursors thereof, in ready to use aqueous oral compositions, such as gels, pastes and the like, and products for reconstitution in water, for use by humans and animals, together with processes for their preparation and uses thereof.

Creatine, also known as creatine monohydrate, is recognized as a valuable amino acid involved in energy buffering within cells that express creatine kinase, especially red muscle cells. Currently, creatine is commercially available in substantially non-aqueous products, typically powders such as Creapure® and solid tablets or bars. Creatine is taken by individuals to increase stamina during exercise and increase recovery speed. Commercially available aqueous products are available but unfavourable levels of the creatine break-down product, creatinine, which is formed due to the instability of creatine in water, have been found in some of them. Current, non-creatine products favoured by distance runners, cyclists, triathlon and decathlon athletes are concentrated nutrition and rehydration gels. These have to be taken separately from creatine products due to the aqueous nature of the gels.

There exists a need, therefore, for oral products comprising creatine that overcome the problems of existing products, e.g. short shelf life due to creatine conversion into creatinine. In particular, there is a need for aqueous creatine products that can be taken directly without need for preparation prior to use. Additionally, there is a need for aqueous creatine products that can be conveniently prepared by the user and stored prior to use avoiding the need for preparation or reconstitution immediately prior to consumption. Such products should provide suitable bioavailability of the creatine for their intended use.

The present invention provides aqueous compositions comprising creatine in convenient, ready to use, pre-packed products, in a form such as gels and pastes, as well as compositions comprising creatine in a form suitable for reconstitution and subsequent storage prior to consumption. It has surprisingly been found that colloidal creatine is stable in the aqueous environments of the compositions of the invention.

Accordingly, the present invention provides an oral composition comprising colloidal creatine, one or more gelling or thickening agents, and 5% to 98.5% weight for weight (w/w) of water.

Colloidal creatine suitable for use in the compositions of the present invention may be suitably prepared by methods such as described in United States Patent Application No. US 2001/0042936.

As used herein, 'creatine' includes creatine, cyclocreatine, phosphocreatine and other forms or analogues thereof that convert to creatine upon ingestion or contact with water, together with any salts thereof and any anhydrate or hydrate of any such creatine compound or salt thereof.

Compositions of the present invention may optionally comprise one or more additional excipients. Preferably, the oral compositions of the present invention comprise a suspension of colloidal creatine.

The oral compositions of the present invention may comprise one or more of the following gelling and/or thickening agents: anionic polysaccharides, modified starch, dextrin, gelatine, alginate, carrageenan (in kappa, iota, or lambda form), gums (e.g. exudate, konjac guar gum, tara gum, locust bean gum, acacia gum; gum arabic, xanthan gum, karaya gum, cassia gum), carbomers, pectin, cellulose, soybean hemicellulose, methyl cellulose, ethyl cellulose, hydroxypropyl cellulose, hydroxypropyl methyl cellulose, ethyl methyl cellulose, carboxy methyl cellulose, cross-linked sodium carboxy methyl cellulose, polysorbates and lecitihins, silicon dioxide.

Preferably, the oral compositions of the present invention comprise a starch based gel or a thixotropic gel.

Preferably, the one or more gelling or thickening agents comprise one or more hydrocolloids or gums or a mixture thereof.

Preferably, the one or more hydrocolloids are independently selected from agar, alginate, arabinoxylan, carrageenan, carboxymethylcellulose, cellulose, curdlan, collagen, animal or vegetable derived gelatin, gellan, beta-glucan, guar gum, gum arabic, locust bean gum, pectin, starch and xanthan gum.

More preferably, the one or more hydrocolloids are independently selected from carrageenan, collagen, animal or vegetable derived gelatin, and xanthan gum. Most preferably, the oral compositions of the present invention comprises carrageenan in combination with calcium acetate and potassium chloride as gelling or thickening agent, optionally together with one or more further gelling or thickening agents.

Typically, the oral compositions of the present invention have a viscosity greater than water at room temperature, preferably greater than approximately 250 centipoise (cP). The upper limit of viscosity is preferably 350,000 centipoise (cP), and most preferably, the viscosity is within the range of 750 to 250,000 (cP).

Preferably, the oral compositions of the present invention are a gel or paste. The compositions of the invention may also be chewable jellies. Gels form the most preferred aspect of the present invention.

Preferably, the colloidal creatine is suspended in an aqueous oral gel.

Aqueous oral gels of the invention are ready to use and may be in any suitable gel-like form like standard gels used in sports nutrition e.g. Viper® Active gels, pastilles, jelly or jelly beans, for example.

The final concentration of gel or gum may preferably be from 0.01% to 90%, depending on the desired viscosity or solid nature of the end product. Preferably, the final concentration of gel or gum may be from 0.05% to 50% and more preferably from 0.1% to 20%. Suitable final upper and lower concentrations and specifically preferred concentrations are 0.05%, 0.1%, 0.5%, 0.75%, 1%, 1.5%, 2%, 2.5%, 3%, 3.5%, 4%, 4.5%, 5%, 5.5%, 6%, 6.5%, 7%, 7.5%, 8%, 8.5%, 9.0%, 9.5%, 10%, 11%, 12%, 13%, 14%%, 15%, 16%, 17%, 18%, 19% and 20%.

In a preferred embodiment, the present invention provides an oral composition comprising colloidal creatine, 0.01% to 20% of one or more gelling or thickening agents, and 5% to 98.5% weight for weight (w/w) of water.

Preferably, the oral compositions of the present invention comprise creatine (2-(methylguanidino)ethanoic acid), creatine monohydrate, cyclocreatine, or phosphocreatine in a colloidal form.

Preferably the colloidal creatine is made using CreaPure®, which is a high purity form of creatine monohydrate available from ALZCHEM®, and is a fine dispersion or molecular dispersion of creatine in a matrix of a physiologically acceptable polymeric binder, as per US2001/0042936A1 and most especially the product sold as Creaphil™.

Preferably, the physiologically acceptable polymeric binder is a thermoplastic polymer. More preferably, the physiologically acceptable polymeric binder is a water-soluble or water-swellable polymer.

Water-soluble or water-swellable physiologically acceptable polymeric binders contain units of hydrophilic monomers, where appropriate in conjunction with units of hydrophobic monomers. They can be assigned, inter alia, to the natural or modified polysaccharides; polyalkylene oxides which are solid at room temperature; homopolymers and copolymers of hydrophilic, ethylenically unsaturated monomers such as N-vinylamides, ethylenically unsaturated mono- and dicarboxylic acids, (meth)acrylamide, hydroxyalkyl(meth)acrylates and the like.

Examples of suitable physiologically acceptable polymeric binders are: polyvinylpyrrolidone (PVP), copolymers of N-vinylpyrrolidone (NVP) and vinyl esters, in particular vinyl acetate, copolymers of vinyl acetate and crotonic acid, partially hydrolyzed polyvinyl acetate, polyvinyl alcohol, poly(hydroxyalkyl acrylates), poly(hydroxyalkyl methacrylates), copolymers of methyl methacrylate and acrylic acid, polyacrylamides, polyethylene glycols, polyvinylformamide (where appropriate partially or completely hydrolyzed), cellulose esters, cellulose ethers, in particular methylcellulose and ethylcellulose, hydroxyalkylcelluloses, in particular hydroxypropylcellulose, hydroxyalkylalkylcelluloses, in particular hydroxypropylethylcellulose, cellulose phthalates, in particular cellulose acetate phthalate and hydroxypropylmethylcellulose phthalate, and mannans, in particular galactomannans. Of these, particular preference is given to polyvinylpyrrolidone, polyethylene glycol, copolymers of N-vinylpyrrolidone and vinyl esters, poly(hydroxyalkyl acrylates), poly(hydroxyalkyl methacrylates), alkylcelluloses and hydroxyalkylcelluloses, especially the polyvinylpyrrolidones and vinylpyrrolidone/vinyl acetate copolymers having the proprietary name Kollidon®.

Binders which are advantageously used as physiologically acceptable polymeric binders are those having a K value (according to Fikentscher, Cellulose-Chemie 13 (1932), p. 58-64, 71-74) in the range between 10 and 100, preferably between 15 and 80, in particular of about 30. The most preferred polyvinylpyrrolidones have a K value in the range between 20 and 60.

More preferably, the physiologically acceptable binder is selected from polyvinylpyrrolidone, polyethylene glycol, copolymers of N-vinylpyrrolidone and vinyl esters, poly(hydroxyalkyl acrylates), poly(hydroxyalkyl methacrylates), alkylcelluloses, hydroxyalkylcelluloses, and mixtures thereof.

Most preferably, the physiologically acceptable binder is hydroxypropyl methylcellulose.

The oral compositions of the present invention may comprise from 5% to 98.5% weight for weight (w/w) of water. More preferably, the water content is from 20% to 90% w/w. Yet more preferably, the water content is from 30% to 80% w/w. Even more preferably, the water content is from 35% to 70% w/w. Preferred lower and upper ranges for the water content (w/w) each independently include 30%, 35%, 40%, 50%, 55%, 60%, 70%, 80%, 82%, 83%, 84%, 85%, 87%, 88%, 89%, 90%, 91%, 92%, 93% or 94%.

Preferably, the oral compositions of the present invention comprise colloidal creatine at weight/weight (w/w) 1 to 60% w/w, more preferably from 2 to 50%, yet more preferably from 4 to 30%, yet more preferably from 5 to 20%, yet more preferably from 7 to 15%, even more preferably from 8 to 10%. Exemplary (w/w) values include 1%, 2%, 4%, 6%, 8%, 10%, 11%, 12%, 12.5% and 15%, 16%, 16.5%, 17%, 17.5%, 18% and 18.5% w/w.

Use of sugars, salts and/or electrolytes may be included to enhance the hydrating effect of oral gels with low amounts of water, e.g. 5% to 15% w/w water content.

The oral compositions of the present invention may additionally contain one or more standard rehydration ingredients selected from electrolytes, bicarbonate precursors, amino acids and energy sources.

Electrolytes include, for example, sodium and potassium salts, such as sodium formate, sodium chloride, sodium acetate and potassium chloride. Bicarbonate precursors include, for example, citric acid and propionic acid. Amino acids include, for example, arginine, glutamine and glycine. Energy sources include, for example, carbohydrates, polysaccharides, monosaccharides and sugars, especially dextrose, sucrose and fructose.

Preferably, the oral compositions of the present invention comprise one or more additional rehydration agents selected from electrolytes and sugars.

Preferably, the $Na^+$ concentration is between 50 and 250 mM, more preferably between 100 mM and 175 mM, yet more preferably between 125 mM and 165 mM and most preferably 140 mM or 150 mM in the oral rehydration product.

Preferably, the oral compositions of the present invention are isotonic.

The oral compositions of the present invention may be any suitable pH that provides or enhances stability or flavour for example. Preferably, the oral compositions of the present invention have a pH in the range of 5 to 8, more preferably from 5.5 to 7.5, and most preferably from 6 to 7.

The oral compositions of the present invention may further comprise one or more stimulants such as caffeine, ginseng, guarana, tyrosine, B Vitamins, especially Vitamin B12 and Gingko.

The oral compositions of the present invention may further comprise one or more creatine uptake stimulants such as Russian Tarragon (*Artemisia dracunculus*).

The oral compositions of the present invention may further comprise one or more poly unsaturated fatty acids, for example alpha linoleic acid, eicosapentaenoic acid or docosahexaenoic acid.

The oral compositions of the present invention may further comprise one or more natural or synthetic antioxidants.

Preferably, the antioxidant comprises one or more plant extracts, especially fruit extracts such as raspberry, blueberry, blackberry and strawberry. These may also act as flavours or flavour enhancers. Exemplary antioxidants can be found in *Michael Ash and Irene Ash, Hand Book of Preservatives.*

More preferably, the antioxidant comprises one or more of Vitamin E, Vitamin C, butylated hydoxyanisole or BHA (E320), butylated hydroxytoluene of BHT (E321), sodium methylparaben, sodium ethylparaben, sodium propylparaben, sodium benzoate, potassium sorbate, sodium ascorbate and NiaSept®. Most preferably, the antioxidant comprises one or more of sodium methylparaben, sodium ethylparaben, sodium propylparaben, sodium benzoate, potassium sorbate, sodium ascorbate and NiaSept®.

Preferably, the oral compositions of the present invention comprise one or more anti-inflammatory agents.

Additionally the oral compositions of the present invention may include standard excipients like acid, acidity regulators, anti-caking agents, anti-foaming agents, bulking agents, carriers and carrier solvents, emulsifiers, firming agents, flavour enhancers, flour treatment agents, foaming agents, glazing agents, humectants, modified starches, packaging gases, propellants, raising agents and sequestrants.

The oral compositions of the present invention may also be used merely to deliver creatine and need not provide any other nutritional benefit.

The oral compositions of the present invention may further comprise one or more ingredients selected from flavourings, flavour enhancers, sweeteners, colourings, stimulants, polyunsaturated fatty acids, antioxidants.

Preferably, the sweeteners are water-soluble sweetening agents such as monosaccharides, disaccharides and polysaccharides such as monosaccharides, disaccharides and polysaccharides or water-soluble artificial sweeteners such as soluble saccharin salts, e.g. (Acesulfame-K).

Most preferably, the sweeteners are one or more of sucrose, dextrose, fructose, sucralose, acesulfame-k, dextrose, saccharine, aspartame, and high fructose corn syrup.

Rehydration and nutritional products may preferably be in the form of gels or pastes, or powders for reconstitution in water, and drinks and such products are used by athletes before, during and after exercise.

Ideally, aqueous energy and recovery products, as used by athletes for example, will contain creatine together with one or more other components of standard rehydration products, for example, maltodextrin, protein (especially whey protein), sugars, and caffeine, sodium (salt), potassium, vitamins (A, C, E, B1, B2, B3, B5, B6, and/or B12), amino acids, fruit juice concentrates, taurine, ginseng, and quercetin.

According to a further aspect of the present invention there is provided the use of colloidal creatine in oral aqueous gels or pastes.

According to a further aspect of the present invention there is provided a method of manufacturing an oral gel that comprises addition of colloidal creatine to the oral rehydration gel mix.

Where the compositions of the invention comprise a gel or paste, these may preferably be sold in a squeeze-able container, in volumes ranging from 25 ml to 100 mls, or in any volume (10 s of mls to liters) bottle or dispenser. The present invention therefore additionally comprises an oral gel or paste product in a squeezable container.

The container may preferably comprise a twist on and off top to allow for multiple uses. Alternatively, the container may comprise a tearable or rip-off segment to allow exit of the gel with one or few squeeze actions, comparable to products commonly called "shots".

Where the compositions of the invention comprise jellies, these may be sold in bags or in blister packs or boxes or dispensers.

The oral compositions of the present invention enable the product to be sold ready for use and enables manufacture, distribution and storage without significant degradation of the active creatine ingredient to inactive derivatives. Preferably, the oral compositions of the present invention possess a creatine half-life of at least 1 month, more preferably 3 months, yet more preferably at least 4 months, yet more preferably at least 6 months and most preferably, at least 12 months. For example, in preferred embodiments, the half-life is at least 180 days.

The oral compositions of the present invention may preferably have a store shelf-life of at least 3 months.

In a further aspect, the present invention provides for the use of colloidal creatine as defined herein in a stable oral gel composition.

According to a further aspect of the present invention there is provided a powder, gel or paste, for reconstitution in water comprising colloidal creatine as defined herein and one or more gelling or thickening agents. Such powders, gels or pastes, may provide additional stability for storage and enable longer product shelf-life. Reconstitution of the product by the user may be done on a scale sufficient to provide a composition that may be used over a period of time, such as 1 or 2 days, or a week or more. The reduced frequency of reconstitution compared with traditional products which require consumption just after preparation has clear benefits. The reconstituted product be stored at room temperature or refrigerated.

The compositions of the present invention as defined herein area also suitable for use in the pharmaceutical or veterinary fields.

The present invention therefore, additionally provides a colloidal creatine composition as defined herein that is an oral pharmaceutical or veterinary composition.

The present invention additionally provides a colloidal creatine composition as defined herein, for use as a medicament.

The present invention additionally provides a colloidal creatine composition as defined herein, for use as a cognitive aid in a human or for use in the treatment of dehydration in a human or animal. Such uses may be for either medical or non-medical purposes.

The present invention additionally provides a method of treating dehydration in a human or animal, or for improving cognition in a human, comprising administering an effective amount of an oral composition comprising colloidal creatine as defined herein. Such methods may be for either medical or non-medical purposes.

The amount of sugar, e.g. fructose, sucrose or dextrose contained in the oral compositions of the present invention may be about 5 to 40%, preferably about 10 to 35%, more preferably about 15 to 30%.

The oral compositions of the present invention may also comprise 0.01 to 0.5% by weight of an emulsifying agent and/or 0.1 to 1% by weight of agar, and 5 to 98.5% by weight of water.

Emulsifiers include glycerin fatty acid esters, phosphatides such as egg yolk lecithin, hydrogenated egg yolk lecithin, soybean lecithin and hydrogenated soybean lecithin; synthetic surfactants such as polyoxyethylene monooleate; sucrose fatty acid esters; sorbitan fatty acid esters; and propylene glycol fatty acid esters.

They can be used in combination. The proportion of emulsifying agent is preferably about 0.01 to 1.5% (w/w), usually between 0.05 to 0.4%.

The present invention additionally provides a process for the preparation of an oral composition as defined herein comprising mixing colloidal creatine, one or more gelling or thickening agents, and water, and optionally one or more further excipients, and heating to between 15 to 70 degrees Celsius.

Preferably, the colloidal creatine is obtained by a process comprising:

a) preparing a mixture which comprises at least one thermoplastic, physiologically tolerated, water-soluble or water-swellable polymeric binder and creatine, and contains 1 to 20 mol of water per mol of creatine, b) plasticating the mixture at or above the softening point of the polymeric binder, c) shaping the plasticated mixture to dosage forms and cooling;

and optionally, the mixture is plasticated with at least partial evaporation of the water, and optionally, the plasticated mixture comprises at least 3.3 mmol of creatine based on the mass of the plasticated mixture.

The present invention additionally provides an oral composition preparable by a process as defined herein.

EXAMPLES

The following examples illustrate the invention.

The colloidal creatine used herein is hydroxypropyl methylcellulose (HPMC) creatine, which may be prepared according to European Patent Application No. EP 1,142,571, also published as United States Patent Application No. US 2001/0042936, and is commercially available from Anglo-Swiss™ Gmbh (Creaphil™).

A thick suspension of the colloidal creatine compound in water (2 to 12 g 20 $mol^{-1}$ of water) is made up before adding it to 180 mls of the commercially available rehydration gel (CARG), in this case Rehydion® from Ceva Sante®, comprising 11.5 g Sodium (sodium acetate and sodium chloride) 4.5 g of potassium (as potassium chloride) and 8.6 g of chloride (as sodium chloride and potassium chloride).

A spectrophotometric scan of the colloidal creatine (10 mg $ml^{-1}$ dissolved in HPLC mobile phase), the CARG (1:15 dilution in HPLC mobile phase) and the HPLC mobile phase was performed to determine the appropriate detection wavelength for the HPLC assay. The scan was performed over a wavelength range from 190-950 nm. It was decided to use 220 nm as the detection wavelength.

Due to the viscous nature of the CARG it had to be diluted by a factor of 10 at the very least before samples could be injected onto the HPLC. In general a dilution factor of 1/15 was used in the analysis of the samples. The variation in peak area over the course of the experiment was not significant and gave a standard deviation of 1351126.18 (approximately equivalent to 0.13 mg $ml^{-1}$ creatine), see Tables 1 and 2.

TABLE 1

HPLC results for gels with colloidal creatine (1:15 dilution).

| Sampling date | Retention Time | Peak area |
| --- | --- | --- |
| 12 Feb. 2011 | 3.15 | 17407146.00 |
| 12 Feb. 2011 | 3.16 | 15844576.00 |
| 12 Feb. 2011 | 3.10 | 13676531.00 |
| 12 Feb. 2011 | 3.16 | 14550719.00 |
| 15 Feb. 2011 | 3.15 | 13312384.00 |
| 24 Feb. 2011 | 3.16 | 14092855.00 |
| 03 Mar. 2011 | 3.17 | 14978398.00 |
| 10 Mar. 2011 | 3.15 | 15812102.00 |

TABLE 2

HPLC results for CARG spiked with 10.0 mg $ml^{-1}$ colloidal creatine.

| Retention Time | Total Peak area (A) | Average peak area due to gel only (B)* | Peak area due to colloidal creatine (A − B) | Equivalent creatine concentration (mg $ml^{-1}$) |
| --- | --- | --- | --- | --- |
| 3.15 | 26283932 | 15369743.00 | 10914189.00 | 10.6 |
| 3.16 | 26178915 | 15369743.00 | 10809172.00 | 10.5 |

Initially, about 9 mg $ml^{-1}$ creatine could be recovered from the gels held under both storage conditions. In the gels held at 20° C., after 2 days the creatine recovery levels fell to between 5.1 and 7.7 mg $ml^{-1}$, and thereafter recovery levels increased until by day 6, 100% recovery was achieved. On average 8 to 10 mg $ml^{-1}$ could be recovered from the gels held at 20° C. over the course of the trial. After 2 days, the creatine recovery level fell to between 5.2 and 6.3 mg $ml^{-1}$ in the gels held at 4° C. After 4 days recovery levels in these gels were between 4.7 and 5.8 mg $m^{-1}$. After 6 days the creatine recovery levels began to increase slowly up until the end of the trial where recovery levels were between 6.0 and 9.8 mg $ml^{-1}$.

Statistical analysis of the results showed that there was a significant difference between the recovery levels of creatine at days 4 and 6 in the gels held at 20° C. or 4° C., with significantly lower levels of creatine recovered from the 4° C. samples. At days 0, 2, 12, 19 and 26 there was no significant difference between the creatine levels recovered from gels held at 20° C. or 4° C.

Recovery of 100% of the creatine was only observed in the samples held at 20° C. after 20 days. Maximum recovery levels of 49 to 55 mg $ml^{-1}$ creatine were observed in samples held at 4° C. and only after 23 days. Statistical analysis of the results showed that there was a significant difference between the recovery levels of creatine after day 2 in the gels held at 20° C. and 4° C.

The results indicated that the creatine was stable within the CARG for up to 26 days when held either at 20° C. or 4° C. (Figure 1).

Under the conditions tested 10 to 20% of the colloidal creatine was not immediately recoverable from the gel. Depending on the storage temperature, 100% recovery was obtained after 6 to 26 days. Gels stored at 20° C. were faster to reach 100% recovery than those stored at 4° C.

These samples were re-tested after 180 days providing the following results: 10 mg/ml gel (room temperature) average=8.42 mg/ml and 10 mg/ml gel (4° C.) average=7.28 mg/ml.

The introduction of the creatine compound into the CARG did not adversely affect the microbiological quality of the gel.

Two aqueous gels, (A) and (B), were created containing colloidal creatine were made by mixing with water and heating to 55 deg Celsius:

(A)

| Excipient | Weight(g) |
| --- | --- |
| Water | 94.69 |
| Colloidal creatine | 5 |
| Lecithin | 0.01 |
| Sodium benzoate | 0.020 |
| Guar Gum | 0.1 |
| Alginate | 0.15 |

(B)

| Excipient | Weight(g) |
|---|---|
| Water, Citrus flavour and colour | 83.735 |
| Lecithin | 0.02 |
| Colloidal creatine | 15 |
| Xanthan Gum | 0.1 |
| Sodium benzoate | 0.020 |
| Alginate | 0.250 |

This was stored in a 100 ml plastic dispensing container at room temperature. Creatine levels were measured after 3 months using the above HPLC method and found to have decreased by 22% at 4 deg Celsius and only 5% at room temperature.

Another oral product was made using colloidal creatine in standard commercially available jelly beans reconstituted in water. The concentrations of colloidal creatine per ml of reconstituted jelly bean were 0, 20, 50, 100 and 200 mg/ml. Phosphocreatine was used in the control group of reconstituted jelly beans, see Table 3:

TABLE 3

| Colloidal creatine (mg) | Jelly liquid (ml) | Final concentration (mg/ml) |
|---|---|---|
| 0.0000 | 45 | 0 |
| 1000.0 | 45 | 20 |
| 2500.0 | 45 | 50 |
| 5000.0 | 45 | 100 |
| 10000.0 | 45 | 200 |

All of these reconstituted jelly beans had a water content of between 60 and 70%.

Reconstituted jelly beans with colloidal creatine were tested at days 1, 6, 9, 12, 16, 19, 44, 55 and 72. After 72 days the reconstituted jelly beans still had 70% to 75% original creatine levels (using HPLC analysis). No creatine was detected in the control reconstituted jelly beans after 72 days.

In another example 11 g animal gelatin and 100 g of glucose was made up to 150 mls with boiling water and dissolved, this was allowed to cool and 6 g of colloidal creatine was added at 50 deg C. The liquid gel was put into 15×10 ml moulds.

A further example, 100 g of colloidal creatine was mixed with sugar, modified corn starch, gelling agents: carrageenan, calcium acetate, potassium chloride; colours: beetroot red, annatto; citric acid, natural flavouring (Greens Quick Gel™ mix) and made up to 250 ml or 300 ml or 350 ml with water at room temperature. This was mixed until a homogeneous suspension was achieved. This was stored at 4 deg C. and proved stable by HPLC, i.e. creatine values after one month were >90% of start levels (Creaphil™ is 72% to 75% creatine, the remainder is HPMC).

As a control, 10 g colloidal creatine in 50 ml water and 10 g creatine in 50 ml water were stored at 4 deg Celsius and room temperature. Both showed a 90% loss of creatine content after one month. A similar loss of creatine was observed in a 0.1% gelatine aqueous gel/suspension, whereas the colloidal creatine equivalent only showed a 90% loss after 1 month at room temperature.

In Another Example:

| Avicel | 3.6 g |
|---|---|
| Sorbitol Liquid | 92 ml |
| Xanthan Gum | 0.6 g |
| Glycerine | 13 ml |
| Nipasept | 0.5 g |
| Propylene glycol | 14 ml |
| Polysorbate 80 | 0.1 g |
| Vanilla flavouring | |
| Colloidal Creatine/Creaphil ™ | 7 g |
| Purified water to | 300 ml |

The ingredients were mixed with water and heated to 45 deg C. until a uniform suspension was achieved (1 hour). This proved stable at room temperature after one month, showing a 10% loss of creatine compared to starting levels.

In a further example, 20 mls of a 40% gel (8 g Creaphil) was added to an off the shelf milk drink, providing a simple way to consume the product.

It has been found that aqueous oral products with 5%, 10%, 20%, 30%, 40%, 50% and as much as 60% w/w colloidal creatine are stable below 25 Deg Celsius.

A human subject consumed a composition of the present invention comprising 90 g of colloidal creatine in 300 mls of carageenan gel, over two days, and the composition was found to be palatable, and the subject reported increased alertness and reduced muscle pain after two days of intense exercise.

The invention claimed is:

1. An oral composition in the form of an aqueous oral gel, comprising:
   3 to 20% weight for weight (w/w) of colloidal creatine;
   0.1 to 0.5% w/w of at least one of a gelling and a thickening agent selected from the group consisting of a hydrocolloid, a gum, and a mixture thereof, the hydrocolloid selected from the group consisting of carrageenan, collagen, animal derived gelatin, guar gum, gum arabic, locust bean gum, pectin, starch and xanthan gum; and
   60 to 94% w/w of water, wherein the colloidal creatine, the at least one of a gelling and a thickening agent, and the water are mixed together or the at least one of a gelling and a thickening agent and the water are mixed and then the colloidal creatine is mixed therein, in either case wherein the colloidal creatine is not added to the water first, and wherein the colloidal creatine is obtained by a process comprising:
   a) preparing a mixture which comprises at least one of a thermoplastic, physiologically tolerated, water-soluble or water-swellable polymeric binder and creatine, and contains 1 to 20 mol of water per mol of creatine,
   b) plasticating the mixture at or above the softening point of the polymeric binder, and
   c) shaping the plasticated mixture to dosage forms and cooling; and wherein:
   the oral composition has a creatine half-life of at least 180 days at and below room temperature at a pH of 5 and is suitable for use in a squeeze-able container or a bottle or dispenser.

2. The oral composition of claim 1, wherein the polymeric binder is hydroxypropyl methylcellulose.

3. The oral composition of claim 1, further comprising at least one ingredient selected from the group consisting of flavorings, protein, flavor enhancers, sweeteners, preservatives, colourings, stimulants, carbohydrates, polyunsaturated fatty acids, and antioxidants.

4. A process for the preparation of an oral composition in the form of an aqueous oral gel, comprising:
   mixing 3 to 20% weight for weight (w/w) of colloidal creatine, 0.1 to 0.5% w/w of at least one of a gelling and a thickening agent, and 60 to 94% w/w of water, wherein the colloidal creatine is not added to the water first, and wherein the at least one of a gelling and a thickening agent is selected from the group consisting of a hydrocolloid, a gum, and a mixture thereof, the hydrocolloid selected from the group consisting of carrageenan, collagen, animal derived gelatin, guar gum, gum arabic, locust bean gum, pectin, starch and xanthan gum; and
   heating the mixture to between 15 to 70 degrees Celsius; wherein the colloidal creatine is obtained by a process comprising:
   a) preparing a mixture which comprises at least one of a thermoplastic, physiologically tolerated, water-soluble or water-swellable polymeric binder and creatine, and contains 1 to 20 mol of water per mol of creatine,
   b) plasticating the mixture at or above the softening point of the polymeric binder, and
   c) shaping the plasticated mixture to dosage forms and cooling; and wherein:
   the oral composition has a creatine half-life of at least 180 days at and below room temperature at a pH of 5 and is suitable for use in a squeeze-able container or a bottle or dispenser.

5. The process of claim 4, further comprising plasticating the mixture with at least partial evaporation of the water.

6. The process of claim 4, wherein the plasticated mixture comprises at least 3.3 mmol of creatine based on the mass of the plasticated mixture.

7. An oral composition in the form of an aqueous oral gel prepared according to the process of claim 4, comprising:
   3 to 20% weight for weight (w/w) of colloidal creatine;
   0.1 to 0.5% w/w of at least one of a gelling and a thickening agent selected from the group consisting of a hydrocolloid, a gum, and a mixture thereof, the hydrocolloid selected from the group consisting of carrageenan, collagen, animal derived gelatin, guar gum, gum arabic, locust bean gum, pectin, starch and xanthan gum; and
   60 to 94% w/w of water.

8. A process for the preparation of an oral composition in the form of an aqueous oral gel, comprising:
   mixing 0.1 to 0.5% weight for weight (w/w) of at least one of a gelling and a thickening agent selected from the group consisting of a hydrocolloid, a gum, and a mixture thereof, the hydrocolloid selected from the group consisting of carrageenan, collagen, animal derived gelatin, guar gum, gum arabic, locust bean gum, pectin, starch and xanthan gum, and 60 to 94% w/w of water and then mixing 3 to 20% w/w of colloidal creatine therein; and
   heating the mixture to between 15 to 70 degrees Celsius; wherein the colloidal creatine is obtained by a process comprising:
   a) preparing a mixture which comprises at least one of a thermoplastic, physiologically tolerated, water-soluble or water-swellable polymeric binder and creatine, and contains 1 to 20 mol of water per mol of creatine,
   b) plasticating the mixture at or above the softening point of the polymeric binder, and
   c) shaping the plasticated mixture to dosage forms and cooling; and wherein:
   the oral composition has a creatine half-life of at least 180 days at and below room temperature at a pH of 5 and is suitable for use in a squeeze-able container or a bottle or dispenser.

9. The process of claim 8, further comprising plasticating the mixture with at least partial evaporation of the water.

10. The process of claim 8, wherein the plasticated mixture comprises at least 3.3 mmol of creatine based on the mass of the plasticated mixture.

11. An oral composition in the form of an aqueous oral gel prepared according to the process of claim 8, comprising:
    3 to 20% weight for weight (w/w) of colloidal creatine;
    0.1 to 0.5% w/w of at least one of a gelling and a thickening agent selected from the group consisting of a hydrocolloid, a gum, and a mixture thereof, the hydrocolloid selected from the group consisting of carrageenan, collagen, animal derived gelatin, guar gum, gum arabic, locust bean gum, pectin, starch and xanthan gum; and
    60 to 94% w/w of water.

12. The oral composition of claim 11, wherein the polymeric binder is hydroxypropyl methylcellulose.

13. The oral composition of claim 11, further comprising at least one ingredient selected from the group consisting of flavorings, protein, flavor enhancers, sweeteners, preservatives, colourings, stimulants, carbohydrates, polyunsaturated fatty acids, and antioxidants.

14. The oral composition of claim 7, wherein the polymeric binder is hydroxypropyl methylcellulose.

15. The oral composition of claim 7, further comprising at least one ingredient selected from the group consisting of flavorings, protein, flavor enhancers, sweeteners, preservatives, colourings, stimulants, carbohydrates, polyunsaturated fatty acids, and antioxidants.

* * * * *